US00PP19774P2

(12) United States Plant Patent
Dümmen

(10) Patent No.: US PP19,774 P2
(45) Date of Patent: Feb. 24, 2009

(54) ***BEGONIA* PLANT NAMED 'BBOLY'**

(50) Latin Name: *Begonia×hiemalis*
Varietal Denomination: BBOLY

(75) Inventor: Tobias Gunter Dümmen, Rheinberg (DE)

(73) Assignee: Begonia Breeders Association B.V., Rijsenhout (NL)

( * ) Notice: Subject to any disclaimer, the term of this patent is extended or adjusted under 35 U.S.C. 154(b) by 0 days.

(21) Appl. No.: 12/074,613

(22) Filed: Mar. 5, 2008

(51) Int. Cl.
*A01H 5/00* (2006.01)

(52) U.S. Cl. ..... Plt./349

(58) Field of Classification Search ..... Plt./349
See application file for complete search history.

*Primary Examiner*—Kent L Bell
(74) *Attorney, Agent, or Firm*—C. A. Whealy

(57) ABSTRACT

A new and distinct cultivar of *Begonia* plant named 'BBOLY', characterized by its compact, upright and mounded plant habit; freely branching habit; numerous double flowers that are bright red in color and held above the foliage; and good postproduction longevity.

1 Drawing Sheet

Botanical designation: *Begonia×hiemalis.*
Cultivar denomination: 'BBOLY'.

BACKGROUND OF THE INVENTION

The present invention relates to a new and distinct cultivar of *Begonia* plant, botanically known as *Begonia×hiemalis,* commercially known as Elatior *Begonia,* and hereinafter referred to by the name 'BBOLY'.

The new *Begonia* is a product of a planned breeding program conducted by the Inventor in Rijsenhout, The Netherlands. The objective of the breeding program was to develop new freely branching *Begonia* cultivars with fully double flowers.

The new *Begonia* originated from a cross-pollination made by the Inventor in April, 2003 of two unnamed proprietary selections of *Begonia×hiemalis,* not patented. The new *Begonia* was discovered and selected by the Inventor from within the progeny of the stated cross-pollination in a controlled environment in a greenhouse in Rijsenhout, The Netherlands during the summer of 2005.

Asexual reproduction of the new *Begonia* by cuttings in a controlled environment in Rijsenhout, the Netherlands since the summer of 2005, has shown that the unique features of this new *Begonia* are stable and reproduced true to type in successive generations.

SUMMARY OF THE INVENTION

The cultivar BBOLY has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'BBOLY'. These characteristics in combination distinguish 'BBOLY' as a new and distinct cultivar of *Begonia:*

1. Compact, upright and mounded plant habit.
2. Freely branching habit.

3. Numerous double flowers that are bright red in color and held above the foliage.
4. Good postproduction longevity.

Plants of the new *Begonia* differ primarily from plants of the parent selections in flower form as plants of the parent selections have fewer tepals per flower.

Plants of the new *Begonia* can also be compared to plants of the cultivar BBVERONICA, disclosed in U.S. Plant Pat. No. 15,224. In side-by-side comparisons conducted in Rijsenhout, The Netherlands, plants of the new *Begonia* differed from plants of the cultivar BBVERONICA in the following characteristics:

1. Plants of the new *Begonia* had more tepals per flower than plants of the cultivar BBVERONICA.
2. Plants of the new *Begonia* and the cultivar BBVERONICA differed in flower color as plants of the cultivar BBVERONICA had dark red-colored flowers.

BRIEF DESCRIPTION OF THE PHOTOGRAPH

The accompanying colored photograph illustrates the overall appearance of the new *Begonia,* showing the colors as true as it is reasonably possible to obtain in colored reproductions of this type. Colors in the photograph may differ slightly from the color values cited in the detailed botanical description which accurately describe the colors of the new *Begonia.* The photograph comprises a side perspective view of a typical flowering plant of 'BBOLY' grown in a container.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following observations and measurements were grown in Rijsenhout, The Netherlands in 13-cm containers and under commercial practice in a glass-covered greenhouse during the spring and summer. During the production of the plants, day and night temperatures ranged from 15° C. to 20° C. and light levels were about 18,000 lux. Plants used for the photograph and the description were about three months from planting.

Botanical classification: *Begonia×hiemalis* cultivar BBOLY.
Commercial classification: Elatior *Begonia.*
Parentage:
*Female, or seed, parent.*—Unnamed proprietary selection of *Begonia×hiemalis,* not patented.
*Male, or pollen, parent.*—Unnamed proprietary selection of *Begonia×hiemalis,* not patented.
Propagation:
*Type.*—By terminal vegetative cuttings.
*Time to initiate roots.*—About two weeks at temperatures of about 20° C.
*Time to produce a rooted young plant.*—About three to five weeks at temperatures of about 20° C.
*Root description.*—Fine, fibrous; plants of the new *Begonia* have not been observed to form tubers.
*Rooting habit.*—Freely branching.
Plant description:
*Plant form.*—Compact, upright and mounded plant habit, inverted triangle; freely branching with good stem and stem base strength. Flowers are double and abundant. Moderate growth rate.
*Plant height.*—About 20 cm to 25 cm.
*Plant width.*—About 25 cm to 30 cm.
*Basal branch description.*—Quantity: Freely basal branching with about five to six basal branches developing per plant. Length: About 9 cm to 13 cm. Diameter: About 1 cm to 3 cm. Texture: Smooth, glabrous. Color: 144B.
*Leaf description.*—Arrangement: Simple, alternate. Length: About 8 cm to 9 cm. Width: About 5 cm to 6 cm. Shape: Roughly deltoid. Apex: Acuminate. Base: Cordate to oblique. Margin: Serrate. Texture, upper and lower surfaces: Smooth, glabrous; velvety. Venation pattern: Palmate. Color: Developing and fully expanded leaves, upper surface: 136A; venation, 138A. Developing and fully expanded leaves, lower surface: 138A; venation, 138C. Petiole length: About 4 cm to 6 cm. Petiole diameter: About 4 mm. Petiole texture, upper and lower surfaces: Smooth, glabrous. Petiole color, upper and lower surfaces: 144C.
Flower description:
*Flowering habit.*—Double flowers with numerous tepals arranged in axillary cymes. Usually five to six open flowers per cyme. Many cymes in flower simultaneously. Flowers positioned upright and outwardly above the foliage. Flowers not fragrant.
*Natural flowering season.*—Plants will flower continuously year round in the greenhouse, however plants flower earlier and more abundantly during the summer in The Netherlands. Good postproduction longevity, flowers last about four weeks on the plant. Flowers persistent.
*Cyme height.*—About 6 cm to 8 cm.
*Cyme diameter.*—About 6 cm to 7 cm.
*Flowers.*—Shape: Oval; rose-like. Diameter: About 4 cm to 5 cm. Depth (height): About 1 cm.
*Flower buds.*—Shape: Ovoid. Length: About 1 cm to 1.5 cm. Diameter: About 2 cm. Color: Close to 42A.
*Tepals.*—Arrangement: Rosette. Quantity per flower: Usually about 10 to 15 per flower. Length: About 2 cm to 3 cm. Width: About 3 cm to 4 cm. Shape: Obovate to rounded. Apex: Rounded, obtuse. Base: Orbicular. Margin: Entire, undulate. Texture, upper and lower surfaces: Smooth, glabrous; satiny. Color: When opening, upper surface: 44A. When opening, lower surface: 42C. Fully opened, upper surface: 44A; color becoming closer to 42A with development. Fully opened, lower surface: 43A.
*Flower bracts.*—Quantity/arrangement: Two, opposite. Shape: Broadly ovate. Apex: Acute. Margin: Entire. Texture, upper and lower surfaces: Glabrous, smooth. Color, upper and lower surfaces: Close to 146C.
*Peduncles.*—Angle: Erect to about 30° to 45° from vertical. Length: About 4 cm to 5 cm. Diameter: About 3 mm to 4 mm. Texture: Smooth, glabrous. Color: 31A.
*Pedicels.*—Angle: About 30° to 45° from the peduncle. Length: About 2 cm to 3 cm. Diameter: About 2 mm to 3 mm. Texture: Smooth, glabrous. Color: Close to 31A.
*Reproductive organs.*—Stamens: None observed. Pistils: None observed.
*Seed/fruit.*—Seed and fruit production have not been observed.
Disease/pest resistance: Resistance to pathogens and pests common to *Begonia* has not been observed.
Temperature tolerance: Plants of the new *Begonia* have been observed to tolerate temperatures from about 10° C. to about 35° C.

It is claimed:

1. A new and distinct *Begonia* plant named 'BBOLY' as illustrated and described.

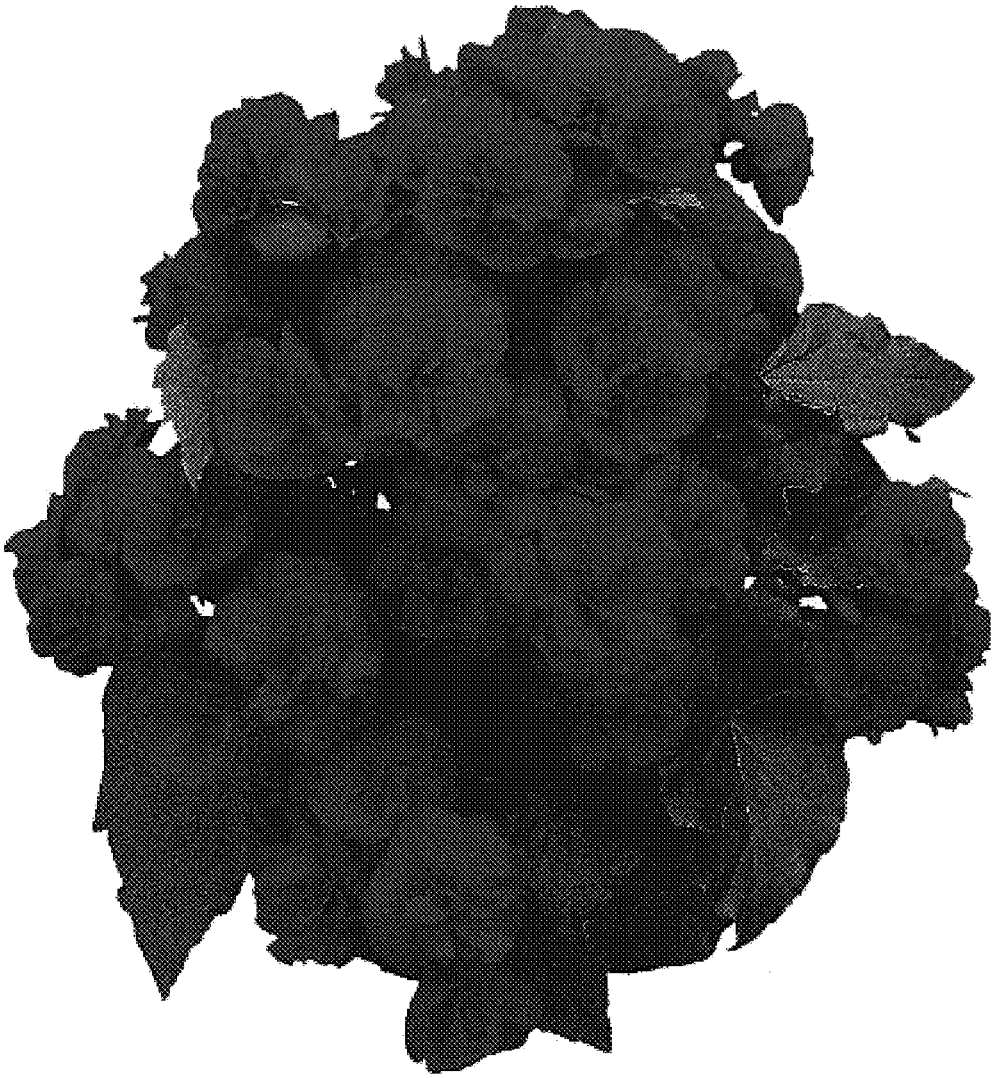

* * * * *